United States Patent
Tian et al.

(10) Patent No.: US 10,598,595 B2
(45) Date of Patent: Mar. 24, 2020

(54) METHOD FOR DETERMINING OIL CONTENTS IN ROCK FORMATIONS

(71) Applicant: PetroChina Company Limited, Beijing (CN)

(72) Inventors: Hua Tian, Beijing (CN); Keyu Liu, Beijing (CN); Caineng Zou, Beijing (CN); Shuichang Zhang, Beijing (CN); Shaobo Liu, Beijing (CN); Xuesong Lu, Beijing (CN); Junjia Fan, Beijing (CN); Xiuli Li, Beijing (CN); Mengjun Zhao, Beijing (CN); Qingong Zhuo, Beijing (CN); Yanjie Gong, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 344 days.

(21) Appl. No.: 15/693,380

(22) Filed: Aug. 31, 2017

(65) Prior Publication Data
US 2018/0059022 A1 Mar. 1, 2018

(30) Foreign Application Priority Data
Aug. 31, 2016 (CN) .......................... 2016 1 07915138

(51) Int. Cl.
*G01N 21/64* (2006.01)
*G01N 33/24* (2006.01)

(52) U.S. Cl.
CPC ............ *G01N 21/64* (2013.01); *G01N 33/241* (2013.01); *G01N 2021/6417* (2013.01); *G01N 2021/6421* (2013.01); *G01N 2201/13* (2013.01)

(58) Field of Classification Search
CPC .................. G01N 21/64; G01N 33/241; G01N 2021/6421; G01N 2021/6417; G01N 2201/13; G01N 21/6402
USPC ........................................................ 250/253
See application file for complete search history.

(56) References Cited

U.S. PATENT DOCUMENTS 9,447,330 B2 * 9/2016 Schlosberg ............ C10G 1/042

FOREIGN PATENT DOCUMENTS

| CN | 1614395 A | 5/2005 |
|---|---|---|
| CN | 100359319 C | 1/2008 |

(Continued)

OTHER PUBLICATIONS

"Determination of bitumen from rocks by chloroform extraction", SY/5118-2005, Measurement of Chloroform extracted Bitumen in Rocks [S], Beijing, Standards Press of China, 2005, 8 pages.

(Continued)

*Primary Examiner* — David P Porta
*Assistant Examiner* — Meenakshi S Sahu
(74) *Attorney, Agent, or Firm* — Hoffman Warnick LLC

(57) ABSTRACT

The invention provides a method for determining oil contents in rocks. The method comprises steps of: measuring a plurality of calibration oil samples having different oil contents, and acquiring a holographic fluorescence spectral intensity corresponding to the calibration oil samples; acquiring a fit relation between the holographic fluorescence spectral intensity and the oil contents of the calibration oil, according to the oil contents of the plurality of calibration oil samples and a plurality of three-dimensional fluorescence spectral intensities corresponding thereto; adding a certain amount of the calibration oil after dilution to rocks to be measured, acquiring a sample of the rocks to be measured and performing a holographic fluorescence measurement of the rock sample to be measured; and introducing the holo- (Continued)

graphic fluorescence spectral intensity of the rock sample to be measured to the fit relation, thus an oil content of the rock sample to be measured is obtained. Accordingly, oil is detectable together with an organic solvent without volatilization of the organic solvent, which not only saves time, but also address a low-detection-limit problem for oil content resulting from volatilization of oil when the organic solvent is volatilized in the conventional method.

16 Claims, 7 Drawing Sheets

(56) References Cited

FOREIGN PATENT DOCUMENTS

| | | |
|---|---|---|
| CN | 103529004 A | 1/2014 |
| CN | 103969235 A | 8/2014 |

OTHER PUBLICATIONS

Chinese First Office Action dated Sep. 19, 2019, for counterpart Chinese patent application No. 201610791513.8, 18 pages.
Chinese Search Report dated Sep. 19, 2019, for counterpart Chinese patent application No. 201610791513.8, 4 pages.
Photochemical Degradation of Petroleum Pollutants in Soil, Chinese Dissertation for the Master Degree Full-test Database, Engineering science section I, Yu Jiahong, pp. 027-32.
Engineering fluid mechanics, metallurgical industry press, Xie Zhenhua, pp. 41-42.

\* cited by examiner

METHOD FOR DETERMINING OIL CONTENTS IN ROCK FORMATIONS

TECHNICAL FIELD

The invention relates to the field of determining oil in rock formations and is suitable for determining oil contents in rocks in the laboratory in fields of petroleum, geology and mining, in particular, a method and device for determining oil contents in rock formations, including mudstone, shale, and tight sandstone and carbonate.

BACKGROUND OF THE INVENTION

At present, a common method in analyzing oil contents in rocks is by measuring chloroform extracted bitumen in rocks (see SY/5118-2005, Measurement of Chloroform extracted Bitumen in Rocks [S], Beijing, Standards Press of China, 2005). In the prior art, oil is extracted from rocks by using an organic solvent and through volatilizing the organic solvent to gain the oil weight by a balance. There exists three major drawbacks in this method: One is its limitation of accuracy of detection, because the method cannot detect an oil quantity with an absolute value of less than 0.001 g or an oil content less than 10 ppm; the other is that a portion of the oil volatilizes during the volatilization of the organic solvent, which may result in a lower measured value of the oil content; it is a more tedious procedure and usually takes a longer time to volatilize the solvent.

SUMMARY OF THE INVENTION

An objective of the invention is to overcome the drawbacks mentioned above, there is provided a simpler method and device for determining an oil content in rocks with a higher precision degree of measurement.

In order to fulfill the above-mentioned objective, the invention concretely provides a method for determining an oil content in rocks, specifically comprising steps of: measuring a plurality of calibration oil samples having different oil contents, and acquiring a holographic fluorescence spectral intensity corresponding to the calibration oil samples; acquiring a fit relation between the holographic fluorescence spectral intensity and the oil contents of the calibration oil, according to the oil contents of the plurality of calibration oil samples and a plurality of holographic fluorescence spectral intensities corresponding thereto; adding a certain amount of the calibration oil after quantitative dilution to rocks to be measured, and acquiring a sample of the rocks to be measured and performing a holographic fluorescence measurement of the rock sample to be measured; and introducing the holographic fluorescence spectral intensity of the rock sample to be measured to the fit relation, thus an oil content of the rock sample to be measured is obtained.

The invention further provides a computer device comprising: a memory, a processor as well as a computer program stored on the memory and runnable on the processor, characterized in that, the processor executes the following steps when executing the computer program: measuring a plurality of calibration oil samples having different oil contents, and acquiring a holographic fluorescence spectral intensity corresponding to the calibration oil samples; acquiring a fit relation between the holographic fluorescence spectral intensity and the oil contents of the calibration oil, according to the oil contents of the plurality of calibration oil samples and a plurality of holographic fluorescence spectrums intensities corresponding thereto; adding a certain amount of the calibration oil after dilution to rocks to be measured, acquiring a sample of the rocks to be measured and performing a holographic fluorescence measurement of the rock sample to be measured; and introducing the holographic fluorescence spectral intensity of the rock sample to be measured to the fit relation, thus an oil content of the rock sample to be measured is obtained.

The invention further provides a computer-readable storage medium, characterized in that, the computer-readable storage medium stores a computer program and the computer program comprises steps of: measuring a plurality of calibration oil samples having different oil contents, and acquiring a holographic fluorescence spectral intensity corresponding to the calibration oil samples; acquiring a fit relation between the holographic fluorescence spectral intensity and the oil contents of the calibration oil, according to the oil contents of the plurality of calibration oil samples and a plurality of holographic fluorescence spectral intensities corresponding thereto; adding a certain amount of the calibration oil after dilution to rocks to be measured, and acquiring a sample of the rocks to be measured and performing a holographic fluorescence measurement of the rock sample to be measured; and introducing the holographic fluorescence spectral intensity of the rock sample to be measured to the fit relation, thus an oil content of the rock sample to be measured is obtained.

Advantageous technical effects of the invention lie in that not only an oil in a trace amount, an oil having a concentration of 10 ppm or lower and an absolute mass of less than 0.001 g can be detected; moreover, an oil is detectable together with an organic solvent without volatilization of the organic solvent, which not only saves time, but also avoids a problem of a lower measured value of the oil content resulting from volatilization of oil when the organic solvent is volatilized.

BRIEF DESCRIPTION OF THE DRAWINGS

The accompanying drawings illustrated herein are provided for a further understanding of the invention, constitute a part of the present application, and are not intended to limit the scope of the present invention and in which.

DETAILED DESCRIPTION OF THE INVENTION

For the sake of clarity of objective, technical solutions and advantages of embodiments of the present invention, the invention will be described in further detail by way of examples with reference to the accompanying drawings. Here, exemplary embodiments and its description are provided by way of explanation of the invention and are not to be construed as limitations of the present invention.

It is demonstrated by facts that oil molecules, after irradiated with light of some wavelength, emit light of slightly longer wavelength than the wavelength, such light is referred to as a fluorescence. A detailed process is that oil molecules when in a ground state and after absorbing light can be transited to an excited state, in which molecules collide with each other and return in a form without loss of radiation energy to a minimum vibration energy level of a first excited state, and the light emitted when molecules at such a vibration energy level return to the ground state is referred to as a fluorescence.

Figure 1:
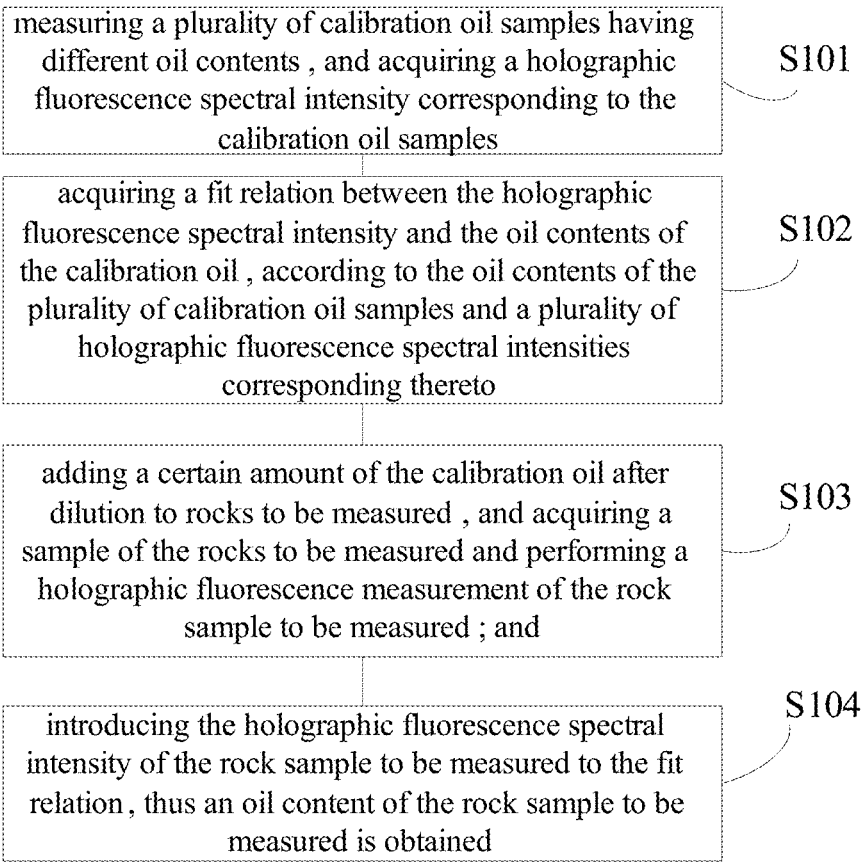
FIG. 1 is a flow diagram illustrating a method for determining oil content in rocks provided in the invention.

On such basis, in order to overcome problems of time consumption of oil-containing measurement in rocks and inaccurate data in the prior art, and is the present invention provides a method for determining an oil content in rocks according to such a feature that oil molecules can issue a specific fluorescence. Referring to FIG. 1, the determination method concretely comprises steps of: S101 measuring a plurality of calibration oil samples having different oil contents, and acquiring a holographic fluorescence spectral intensity corresponding to the calibration oil samples; S102 acquiring a fit relation between the holographic fluorescence spectral intensity and the oil contents of the calibration oil, according to the oil contents of the plurality of calibration oil samples and a plurality of holographic fluorescence spectral intensities corresponding thereto; S103 adding a certain amount of the calibration oil after dilution to rocks to be measured, and acquiring a sample of the rocks to be measured and performing a holographic fluorescence measurement of the rock sample to be measured; and S104 introducing the holographic fluorescence spectral intensity of the rock sample to be measured to the fit relation, thus an oil content of the rock sample to be measured is obtained; wherein the rock sample to be measured includes an organic solvent and rocks to be measured; the holographic fluorescence measurement refers to a three-dimensional fluorescence measurement, and the resulting holographic fluorescence spectral intensity is indicative of a three-dimensional fluorescence spectral intensity; an emission wavelength of the holographic fluorescence measurement ranges from 300 nm to 600 nm and a oil concentration of the certain amount of the calibration oil after dilution ranges from 0 to 10 ppm.

Further, in this embodiment, in order to further improve accuracy and measurement efficiency of the oil content of the rock sample to be measured, a holographic fluorescence measurement is taken in step S103 and a particular value of a holographic fluorescence measurement structure is brought into a fit relation for calculation as needed, thus in practice, experimenters can accurately determine whether data are distorted according to figures of holographic fluorescence measurement result and extract a more accurate particular value (e.g., a peak value is namely a maximum holographic fluorescence spectral intensity) as a final measurement result, further bring it into the fit relation according to the measurement result to obtain more accurate experimental data; simultaneously, a larger emission spectral scope (wavelength ranging from 300 nm to 600 nm) can also be used in use of the holographic fluorescence measurement to obtain more fully data and a broader detection range.

Illustratively, the rock samples of higher oil content have excessive concentration, for example, when the oil concentration is 10 ppm or more, a quenching phenomenon easily occurs, that is to say, the fluorescence intensity is not in the linear relation with oil contents, and as the oil content concentration increases, a phenomenon of decrease in fluorescence intensity arises; to this end, the calibration oil is further quantitatively diluted in the step S103 of the embodiment mentioned above, and the holographic fluorescence measurement is carried out of the rock to be measured for which the calibration oil after dilution is added, so that any measurement error resulting from the quenching phenomenon is effectively prevented.

Figure 4A:
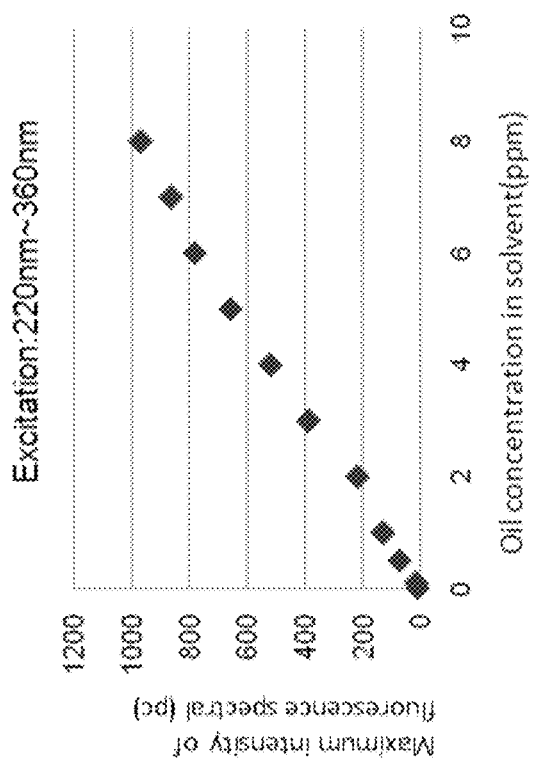
FIG. 4A and FIG. 4B are schematic diagrams illustrating a spectral graph obtained in the method for determining oil content in rocks provided in the invention vs an existing spectral graph obtained by calculation.
Figure 4A:
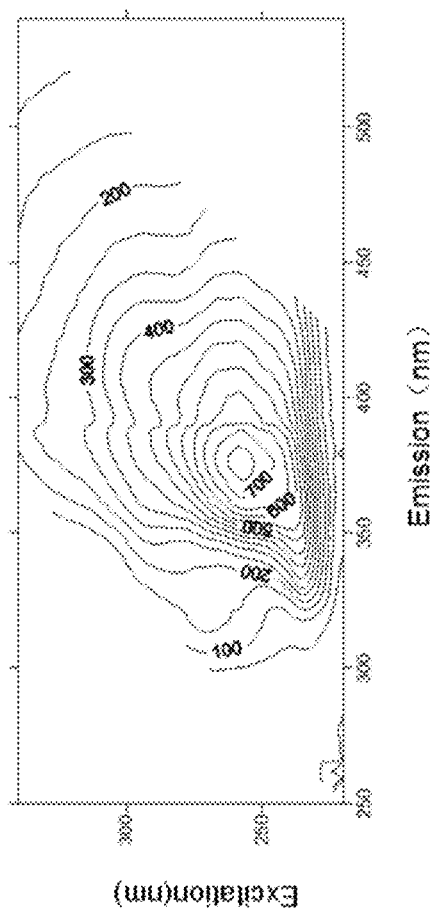
Figure 4B:
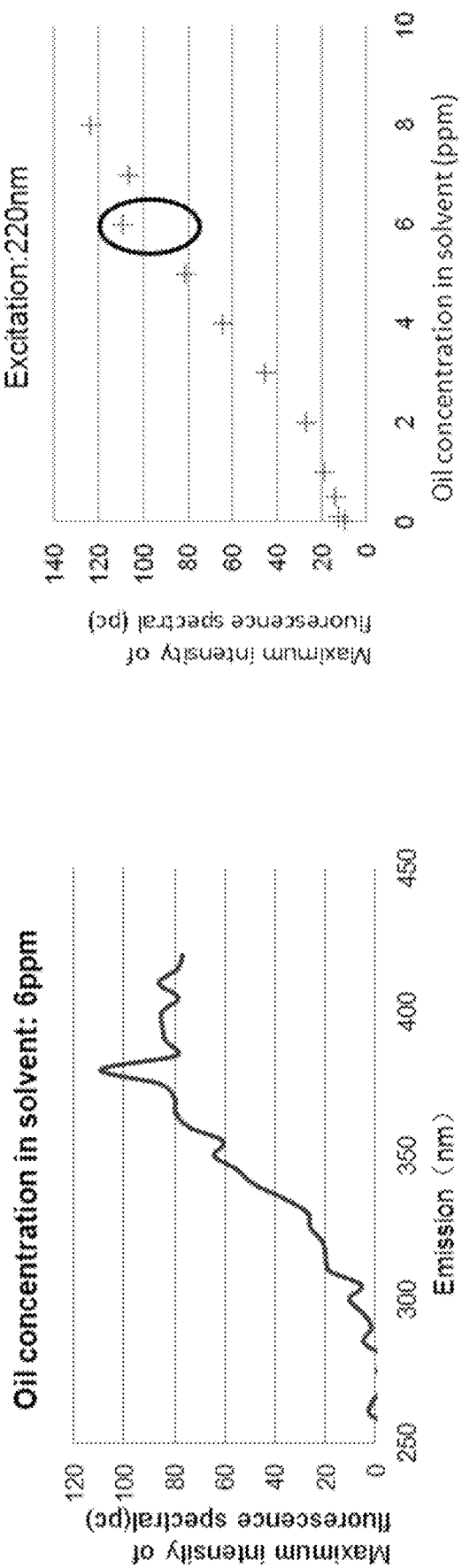

For purposes of illustrating advantages of the above-mentioned embodiments more clearly, referring to FIG. 4A and FIG. 4B below, the holographic fluorescence measurement employed in the present invention is further illustrated as follows:

Referring to FIG. 4A, as illustrated in a three-dimensional fluorescence spectrum figure in combination with data in Table 1 below, there are provided fluorescence spectrum figures obtained using the prior art and the method for determining the oil content of rocks given in the present invention when oil concentration is no more than 8 ppm, wherein the fluorescence spectral figure is on the left of FIG. 4A, and a schematic diagram illustrating a linear relationship between the oil concentration and the fluorescence spectral is on the right of FIG. 4A; it can be seen from the right of the figure that a preferable linear relationship is obtained by adopting the method provided in the present invention; and it can be also seen from the fluorescence spectral figure and linear relationship schematic diagram obtained in the prior art with reference to FIG. 4B that on the right of FIG. 4B, when the concentration is 6 ppm, a distortion is visible, the solution provided in the prior art does not possess a good linear relationship, therefore in practice, the oil content in rocks can be more accurately obtained by adopting the method for determining the oil content in rocks provided in the present invention and an occurrence of a problem of measurement data being inconsistent with actual conditions is avoided.

TABLE 1

| Oil concentration in solvent (ppm) | Maximum intensity of fluorescence spectral (pc) Excitation: 220 nm~360 nm | Maximum intensity of fluorescence spectral (pc) Excitation: 220 nm |
|---|---|---|
| 0.01 | 9.8 | 9.84 |
| 0.1 | 15.0 | 12.5 |
| 0.5 | 72.5 | 13.84 |
| 1 | 129.0 | 19.1 |
| 2 | 217.7 | 27.05 |
| 3 | 388.6 | 45.39 |
| 4 | 520.5 | 64.64 |
| 5 | 658.0 | 81.39 |
| 6 | 782.2 | 109.4 |
| 7 | 864.6 | 106.41 |
| 8 | 970.7 | 123.67 |

Figure 5A:
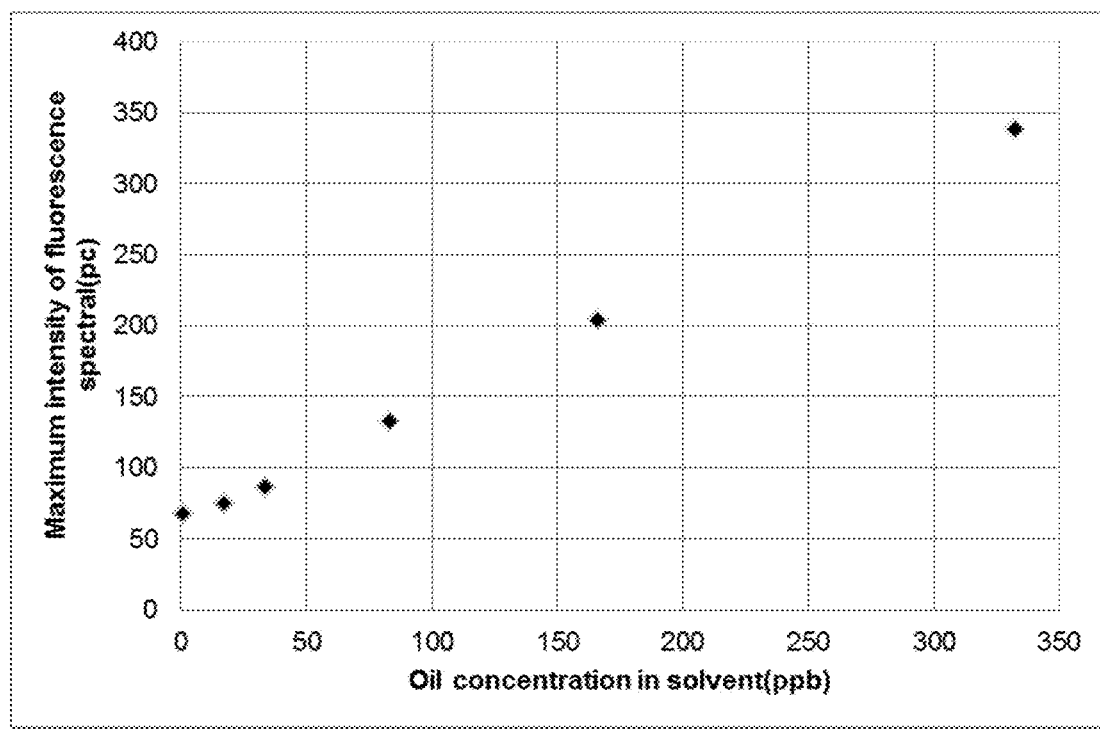
FIG. 5A and FIG. 5B are schematic diagrams illustrating a linear relationship between the oil concentration and fluorescence spectral intensity provided in one embodiment of the invention.
Figure 5B:
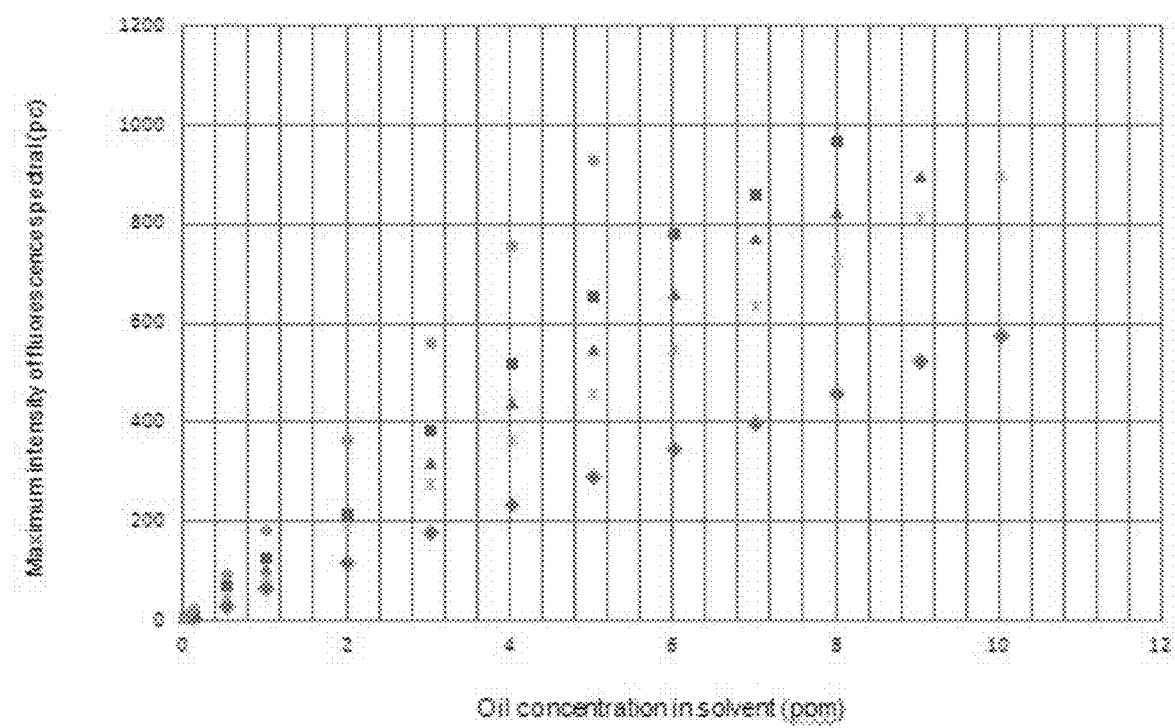

Further referring to FIG. 5A to FIG. 5B, FIG. 5A is a schematic diagram illustrating a relationship between the oil concentration and the fluorescence spectral signals when the oil concentration is 350 ppb or lower, and FIG. 5B is a schematic diagram illustrating a relationship between the oil concentration and the fluorescence spectral signals when the oil concentration is 10 ppm or lower, it can be seen from those figures that a preferable linear relationship is respectively illustrated between the oil concentration under various concentrations and the fluorescence spectral, and the holographic fluorescence spectral is used as an indicator of the oil concentration with markedly higher accuracy.

In one preferred embodiment of the invention, a database can be built according to the corresponding relation of the oil content of the above-mentioned rock sample to be measured uses the holographic fluorescence spectral intensity of the rock sample to be measured. In this embodiment, in view of differences between the holographic fluorescence data detected by different holographic fluorescent instruments, in order to save comparison time during late stages and improve efficiency of experiments, the model information of a holographic fluorescence tester for measuring the rock sample to be measured can also be bound to the holographic fluorescence spectral intensity of the rock sample to be measured and the oil content, and then stored to a database, when the rock sample to be measured is detected during late stages, the oil content of the rock sample to be measured can be directly acquired from the database according to the holographic fluorescence spectral intensity of the rock sample to be measured, wherein the holographic fluorescence tester comprises: Varian Cary Eclipse, HORIBA and Brooker holographic fluorescence instrument and the like.

Wherein the fit relation is given as follows: $I = a \cdot C + I_b$;

where $I_b$ is indicative of a holographic fluorescence spectral intensity of a calibration oil sample having an oil content of 0; C is indicative of an oil content of the current calibration oil sample; I is indicative of a holographic fluorescence spectral intensity of the current calibration oil sample; and a is indicative of a linear fit constant.

In the above-mentioned method for determining the oil content in rocks, the calibration oil sample is an oil-containing organic solvent for which the oil sample to be measured and an organic solvent are blended in ratios. Personnel can allow for synthesis of a plurality of calibration oil samples having different oil contents by blending an oil sample to be measured with an organic solvent in different ratios when configuring calibration oil samples during early stages, and perform a test of holographic fluorescence spectral intensity for those calibration oil samples, respectively, i.e., the holographic fluorescence spectral intensity corresponding to the calibration oil samples having different oil contents can be acquired, wherein the organic solvent may be dichloromethane. Those skilled in the art should be aware that the solvent being dichloromethane is illustrated by way of example only, and the organic solvent is not limited in the present invention.

in the above-mentioned method for determining the oil content in rocks, the method further comprises step of: obtaining an oil-containing volume of the rock sample to be measured according to the following equation: $V_o = B \cdot C_o / V_1$;

where $V_o$ is indicative of an oil-containing volume of the rock sample to be measured (mL); $V_1$ is indicative of a volume of extract of the organic solvent for the rock (mL); and B is an coefficient determined by the mass of the rock sample and volume of the organic solvent.

Obtaining an oil saturation of the rock sample to be measured according to the following equation: $S_o = V_o / M_r / \rho_b \cdot \Phi) \cdot 100\%$;

where $S_o$ is indicative of an oil saturation of the rock sample; $\rho_b$ is indicative of an apparent density of rocks (g/cm$^3$); $\Phi$ is indicative of a porosity of rocks; $V_o$ is indicative of an oil-containing volume of the rock sample to be measured (mL); and $M_r$ is indicative of mass of the rock sample to be measured.

The method for determining the oil content in rocks provided in the present invention is briefly illustrated with reference to the following specific instances, the present invention uses the holographic fluorescence spectral produced by oil molecule aromatic hydrocarbon components in the fluorescence tester as a basis of determination, and a size of intensity of the holographic fluorescence spectral is directly proportional to the oil content in rocks. The calibration oil of known oil content is used as a standard sample, the intensity of the holographic fluorescence spectral thereof is measured, the intensity of the holographic fluorescence spectral of oil-containing organic solvents of unknown content is further measured under the same condition, and the oil content of the oil-containing organic solvents can be obtained by comparing the above two.

Specific steps are provided as follows:

Step (1): conducting a plurality of measurements of a maximum blank holographic fluorescence spectral intensity of an instrument, making statistics for the holographic fluorescence spectral intensity, and determining a spectral standard value ($I_b$);

Step (2): selecting an oil sample to be measured, carrying out a holographic fluorescence spectral measurement with an oil-containing organic solvent ($C_1, C_2 \ldots C_n$, $n \geq 3$, $C_n > 0$) of a different content blended with an organic solvent, and recording the corresponding maximum holographic fluorescence spectral intensities ($I_1, I_2 \ldots I_n$);

Step (3): performing a linear fit of the data obtained in the step (2) to obtain a value in the formula (1);

Step (4): selecting a specific weight, e.g., 0.1 g of the rock sample to be measured, measuring mass $M_r$, introducing it into 10 mL organic solvents, ultrasounding for 3 times each for 15 min;

Step (5): standing for T hours, taking a volume V1 out, placing it into an assay dish and adding 3 mL organic solvents, where the V1 varies according to types of rock, taking calculated values ranging from 10 microliters to 500 microliters according to table 2. The amount of V1 is a key step to make sure the measured results of Co is within the linear range of the linear fit got in step (3). We determine the range of V1 by the reference of porosity of the sample, as the corresponding relation between porosity and V1 value are shown in table 2 (assuming Mr=0.1 g, the oil saturation is 100%, and the porosity of samples is below 30%). The maximum porosity of sample we get is 30%, so the minimum value of V1 is 10 microliters, then as porosity turns lower, bigger V1 value can used. In addition, the oil concentration is in ppb and ppm levels, and it should be defined not more than the maximum detection range of the instrument;

TABLE 2

| Porosity of rock sample (%) | V$_1$ (microliters) | Measured C$_o$ (ppm) |
|---|---|---|
| 30 | 10 | 10 |
| 10 | 10 | 3 |
| 1 | 100 | 3 |
| 0.1 | 500 | 1.5 |

Step (6): placing the assay dish in the holographic fluorescence spectrometer for testing, determining the maximum holographic fluorescence spectral intensity $I_o$, and calculating the content of oil $C_o$ in the sample according to the formula (2) after being converted from the formula (1);

Step (7): calculating the oil-containing volume $V_o$ according to the formula (3) provided in the present invention, and calculating the oil saturation $S_o$ according to the formula (4) provided in the present invention; and Step (8): measuring next sample to be measured and repeating the steps 4 through 7.

The above-mentioned formulas 1 through 7 are concretely shown as follows:

$$I = a \cdot C + I_b \qquad \text{Formula (1)}$$

$$C_o = (I_o - I_b)/a \qquad \text{Formula (2)}$$

$V_o = 30 \cdot C_o/V_1$                 Formula (3)

$S_o = V_o/(M_r/\rho_b \cdot \Phi) \cdot 100\%$        Formula (4)

where $\rho_b$ is indicative of an apparent density of rocks (g/cm³); and $\Phi$ is indicative of a porosity of rocks (%).

Figure 3:
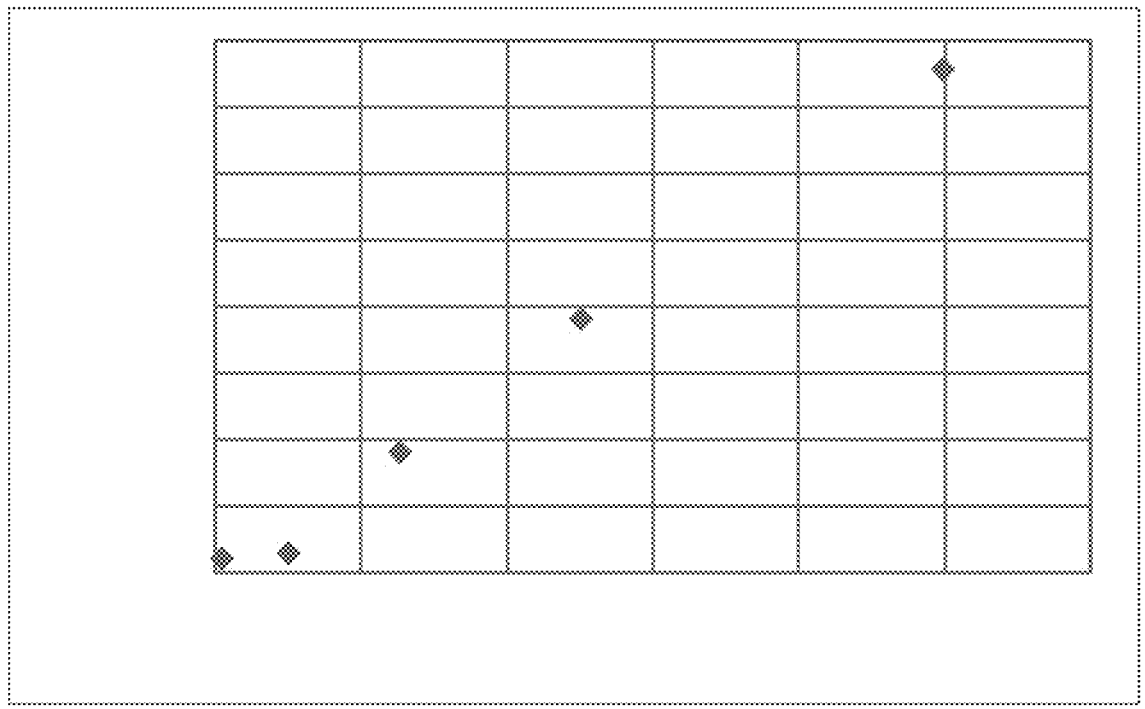
FIG. 3 is a fitting curve of a value for a calibration line in the method for determining an oil content in rocks provided in the invention.

According to the above-mentioned steps, in one embodiment, the present invention uses one tight oil reservoir sample for oil-content measurement, comprising concretely steps of:

Step (1): conducting a plurality of measurements of blank semaphore of an instrument, making statistics for the holographic fluorescence spectral intensity, and determining a spectral standard value ($I_b = -5.700$);

Step (2): selecting 0.01 g of the reservoir oil sample as collected, performing a holographic fluorescence spectrometry of oil-containing organic solvents of different contents ($C_1, C_2 \ldots C_n$, n≥3, $C_n > 0$) blended with organic solvents, and recording the corresponding maximum holographic fluorescence spectral intensities ($I_1, I_2 \ldots I_n$) as shown in Table 3;

Step (3): performing a linear fit of the data obtained in the step (2) to obtain a=38.365 in the formula (1) (see FIG. 3);

Step (4): selecting about 0.1 g of the rock sample to be measured, measuring mass $M_r$=0.1158 g, introducing it into 10 mL organic solvents (including but not limited to dichloromethane), ultrasounding for 3 times each for 15 min;

Step (5): put aside for 1 hours, remove 0.08 mL of the organic solvent for the rock into the analytical dish and add the 3 mL of organic solvent;

determination of the T: $C_o$ will increase with increasing T, and it tends to be stable more than 1 hour; and 1 hour is generally taken for ease of comparison.

determination of the $V_1$: generally taking 0.01 mL of the $V_1$ that is directly proportional with the measured values of $C_o$ and $I_o$, respectively, and adjusting the $V_1$ according to the measured value of the $C_o$<10 ppm and the measured value of the $I_o$<1000;

Step (6): placing the assay dish in the holographic fluorescence spectrometer for testing, measuring the maximum holographic fluorescence spectral intensity $I_o$=93.798, and calculating the content of oil $C_o$=2.59 ppm in the sample according to the formula (2); and Step (7): calculating the oil-containing volume $V_o$=0.00097 mL according to the formula (3) and calculating the oil saturation $S_o$=46% according to the formula (4);

Formulas are illustrated as follows:

$I = 38.365 \cdot C - 5.700$            Formula (1)

$C_o = (93.798 + 5.700)/38.365 = 2.59 \times 10^{-6}$      Formula (2)

$V_o = 30 \cdot C_o/V_1 = 30 \times 2.59 \times 10^{-6}/0.08 = 0.00097$      Formula (3)

$S_o = V_o/(M_r/\rho_b \cdot \Phi) \cdot 100\% = 0.00097/(0.1158/2.75 \times 0.05) \times 100\% = 46\%$      Formula (4)

where $\rho_b$ is 2.75 indicative of an apparent density of rocks (g/cm³); and $\Phi$ is 5.0 indicative of a porosity of rocks (%).

TABLE 3

| Oil content $C_n$ (ppm) | Maximum holographic fluorescence spectral intensity $I_n$ (pc) |
|---|---|
| 0.1 | 10.5 |
| 1.0 | 15.3 |
| 2.5 | 92.1 |
| 5 | 190.1 |
| 10 | 377.1 |

Figure 2:
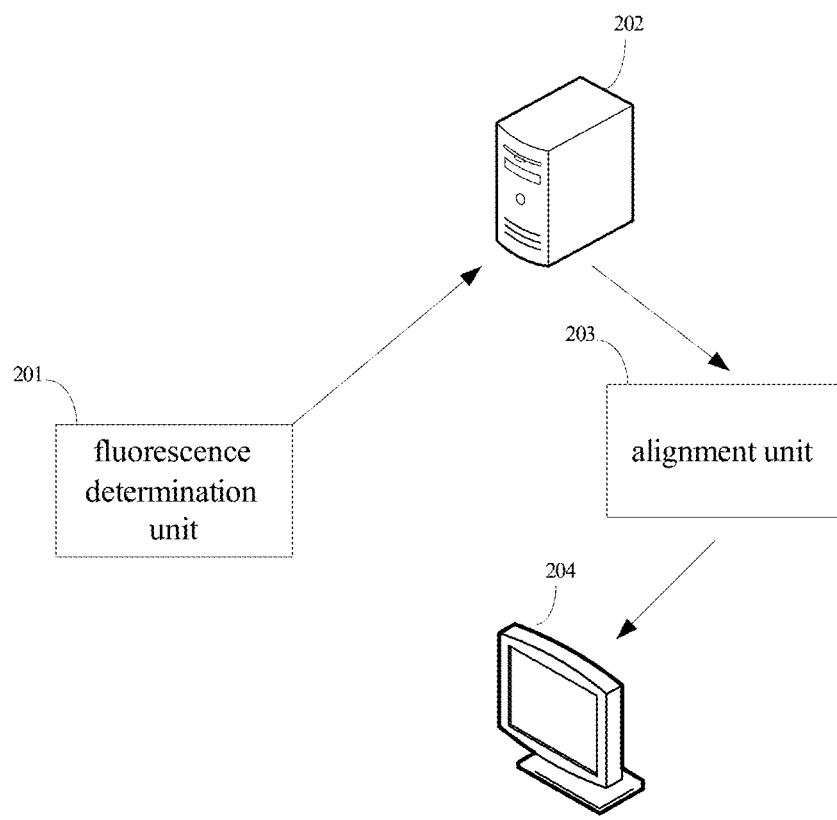
FIG. 2 is a functional module diagram illustrating a device for determining oil content in rocks provided in the invention.

The present invention further provides a device for determining an oil content in rocks. Referring to FIG. 2, the determination device specifically comprises: a fluorescence determination unit 201 for determining a plurality of calibration oil samples having different oil contents and acquiring a holographic fluorescence spectral intensity corresponding to the calibration oil samples; a processing unit 202 for acquiring a fit relation between the holographic fluorescence spectral intensity and the oil contents of the calibration oil, according to the oil contents of the plurality of calibration oil samples and a plurality of holographic fluorescence spectral intensities corresponding thereto; an alignment unit 203 for adding a certain amount of the calibration oil after dilution to rocks to be measured, acquiring a sample of the rocks to be measured and performing a holographic fluorescence measurement of the rocks sample to be measured;

a calculating unit 204 for introducing the holographic fluorescence spectral intensity of the rocks sample to be measured to the fit relation, thus an oil content of the rock sample to be measured is obtained. Further, the processing unit further comprises a memory module that is used to store the fit relation.

In the above-mentioned determination device, the fluorescence measurement unit 201 can be a particle fluorescence analyzer made in Australia; and the processing unit 202 and the calculating unit 204 can be integrated into a processing chip or a computer, and the present invention, however, is not thereby limited.

In one preferred embodiment of the invention, there is further provided a computer device comprising: a memory, a processor as well as a computer program stored on the memory and runnable on the processor, and the processor executes the following steps when executing the computer program: measuring a plurality of calibration oil samples having different oil contents, and acquiring a holographic fluorescence spectral intensity corresponding to the calibration oil samples; acquiring a fit relation between the holographic fluorescence spectral intensity and the oil contents of the calibration oil, according to the oil contents of the plurality of calibration oil samples and a plurality of holographic fluorescence spectral intensities corresponding thereto; adding a certain amount of the calibration oil after dilution to rocks to be measured, and acquiring a sample of the rocks to be measured and performing a holographic fluorescence measurement of the rock sample to be measured; and introducing the holographic fluorescence spectral intensity of the rock sample to be measured to the fit relation, thus an oil content of the rock sample to be measured is obtained.

In one preferred embodiment of the invention, the processor further performs the following steps when executing the computer program: binding the model information of a holographic fluorescence tester for measuring the rock sample to be measured to the holographic fluorescence spectral intensity of the rock sample to be measured and the oil content, then storing to a database.

In the above-described embodiments, the fit relation is given as follows:

$I = a \cdot C + I_b$;

where $I_b$ is indicative of a holographic fluorescence spectral intensity of a calibration oil sample having an oil content of 0; C is indicative of an oil content of the current calibration oil sample; I is indicative of a holographic fluorescence spectral intensity of the current calibration oil sample; and a is indicative of a linear fit constant.

In one preferred embodiment of the invention, the processor further executes the following steps when executing the computer program: obtaining the oil saturation of the rock sample to be measured according to the following equation:

$$S_o = V_o/(M_r/\rho_b \cdot \Phi) \cdot 100\%;$$

where $S_o$ is indicative of an oil saturation of the rock sample; $\rho_b$ is indicative of an apparent density of rocks (g/cm³); $\Phi$ is indicative of a porosity of rocks; $V_o$ is indicative of an oil-containing volume of the rock sample to be measured (mL); and $M_r$ is indicative of mass of the rock sample to be measured.

In one preferred embodiment of the invention, there is further provided a computer-readable storage medium, the computer-readable recording medium stores a computer program and the computer program comprises steps of: measuring a plurality of calibration oil samples having different oil contents, and acquiring a holographic fluorescence spectral intensity corresponding to the calibration oil samples; acquiring a fit relation between the holographic fluorescence spectral intensity and the oil contents of the calibration oil, according to the oil contents of the plurality of calibration oil samples and a plurality of holographic fluorescence spectral intensities corresponding thereto; adding a certain amount of the calibration oil after dilution to rocks to be measured, and acquiring a sample of the rocks to be measured and performing a holographic fluorescence measurement of the rock sample to be measured; and introducing the holographic fluorescence spectral intensity of the rock sample to be measured to the fit relation, thus an oil content of the rock sample to be measured is obtained.

It should be understood by those skilled in the art that the embodiments of the invention can be provided as method, system or computer program product. Therefore, the present invention can use such forms as embodiments for hardware alone, embodiments for software alone or embodiments combining software with hardware. Moreover, the present invention can use forms for the computer program product implemented in one or more computer-usable storage media including computer-usable program codes (including but not limited to magnetic disk storage, CD-ROM, optical memory, etc.) therein.

The present invention is described with reference to the flow diagram and/or block diagram according to the method, device (system) and computer program product in the embodiments of the present invention. It should be understood that each flow and/or block in the flow diagram and/or block diagram and a combination of the flow and/or block in the flow diagram and/or block diagram are implementable by computer program instructions. These computer program instructions can be provided to a processor of a general-purpose computer, a special-purpose computer, an embedded processor or other programmable data processing devices to produce a machine so that the instructions executed by a processor of a computer or other programmable data processing devices produce a device used in realizing the functions specified in one or more flows of the flow diagram and/or one or more blocks of the block diagram.

These computer program instructions may be alternatively stored in a computer-readable memory that can guide a computer or other programmable data processing devices for operations in a particular manner, so that instructions stored in the computer-readable memory produce articles of manufacture that include command devices, wherein the command devices realize the functions specified in one or more flows of the flow diagram and/or one or more blocks of the block diagram.

These computer program instructions can be also loaded into a computer or other programmable data processing devices, thus a series of operation steps are performed on the computer or other programmable devices to produce a processing implemented by the computer, so that the instructions executed on the computer or other programmable devices provide steps used to realize the functions specified in one or more flows of the flow diagram and/or one or more blocks of the block diagram.

The objective, technical solutions and advantageous effects of the present invention are further described in detail with reference to the particular embodiments described above; it should be understood that particular embodiments of the present invention are only recited in the foregoing and are not meant to limit the protection scope of the invention. It is intended that the invention be construed as including all such modifications and alterations insofar as they come within the scope of the appended claims or the equivalents thereof.

The invention claimed is:

1. A method for determining oil contents in rocks, characterized by comprising steps of:
   measuring a plurality of calibration oil samples having different oil contents, and acquiring a holographic fluorescence spectral intensity corresponding to the calibration oil samples;
   acquiring a fit relation between the holographic fluorescence spectral intensity and the oil contents of the calibration oil, according to the oil contents of the plurality of calibration oil samples and a plurality of holographic fluorescence spectral intensities corresponding thereto;
   adding a certain amount of the calibration oil after dilution to rocks to be measured, and acquiring a sample of the rocks to be measured and performing a holographic fluorescence measurement of the rock sample to be measured; and
   introducing the holographic fluorescence spectral intensity of the rock sample to be measured to the fit relation, thus an oil content of the rock sample to be measured is obtained.

2. The method for determining the oil content in rocks according to claim 1, characterized in that, the holographic fluorescence measurement refers to a three-dimensional fluorescence spectrum measurement, and the resulting holographic fluorescence spectral intensity is indicative of a three-dimensional fluorescence spectral intensity.

3. The method for determining the oil content in rocks according to claim 1, characterized in that, an emission wavelength of the holographic fluorescence measurement ranges from 300 nm to 600 nm and an excitation wavelength ranges from 220 nm to 360 nm.

4. The method for determining the oil content in rocks according to claim 1, characterized by further comprising step of: binding the model information of a holographic fluorescence tester for measuring the rock sample to be measured to the holographic fluorescence spectral intensity of the rock sample to be measured and the oil content, then storing to a database.

5. The method for determining the oil content in rocks according to claim 1, characterized in that, the fit relation is given as follows:

$$I = a \cdot C + I_b;$$

where $I_b$ is indicative of a holographic fluorescence spectral intensity of a calibration oil sample having an oil content of 0; C is indicative of an oil content of the current calibration oil sample; I is indicative of a holographic fluorescence spectral intensity of the current calibration oil sample; and a is indicative of a linear fit constant.

6. The method for determining the oil content in rocks according to claim 1, characterized in that, the calibration oil sample is an oil-containing organic solvent for which the oil sample to be measured and an organic solvent are blended in ratios.

7. The method for determining the oil content in rocks according to claim 6, characterized in that, the organic solvent contains dichloromethane.

8. The method for determining the oil content in rocks according to claim 6, characterized in that, a oil concentration of the certain amount of the calibration oil after quantitative dilution ranges from 0 to 10 ppm.

9. The method for determining the oil content in rocks according to claim 1, characterized by further comprising a step of obtaining an oil-containing volume of the rock sample to be measured according to the following equation:

$$V_o = B \cdot C_o / V_1;$$

where $V_o$ is indicative of an oil-containing volume of the rock sample to be measured (mL); $V_1$ is indicative of a volume of extract of the organic solvent for the rock (mL); and B is an coefficient determined by the mass of the rock sample and volume of the organic solvent.

10. The method for determining the oil content in rocks according to claim 1, characterized by further comprising a step of obtaining an oil saturation of the rock sample to be measured according to the following equation:

$$S_o = V_o / (M_r / \rho_b \cdot \Phi) \cdot 100\%;$$

where $S_o$ is indicative of an oil saturation of the rock sample; $\rho_b$ is indicative of an apparent density of the rock (g/cm$^3$); $\Phi$ is indicative of a porosity of the rock; $V_o$ is indicative of an oil-containing volume of the rock sample to be measured (mL); and $M_r$ is indicative of mass of the rock sample to be measured.

11. The method for determining the oil content in rocks according to claim 1, characterized in that, the rock sample to be measured contains the organic solvent and the rocks to be measured.

12. A computer device comprising: a memory, a processor as well as a computer program stored on the memory and runnable on the processor, characterized in that, the processor executes the following steps when executing the computer program:

measuring a plurality of calibration oil samples having different oil contents, and acquiring a holographic fluorescence spectral intensity corresponding to the calibration oil samples;

acquiring a fit relation between the holographic fluorescence spectral intensity and the oil contents of the calibration oil, according to the oil contents of the plurality of calibration oil samples and a plurality of holographic fluorescence spectral intensities corresponding thereto;

adding a certain amount of the calibration oil after dilution to rocks to be measured, and acquiring a sample of the rocks to be measured and performing a holographic fluorescence measurement of the rock sample to be measured; and introducing the holographic fluorescence spectral intensity of the rock sample to be measured to the fit relation, thus an oil content of the rock sample to be measured is obtained.

13. The computer device according to claim 12, characterized in that, the processor further performs the following steps when executing the computer program: binding the model information of a holographic fluorescence tester for measuring the rock sample to be measured to the holographic fluorescence spectral intensity of the rock sample to be measured and the oil content, then storing to a database.

14. The computer device according to claim 12, characterized in that, the fit relation is given as follows:

$$I = a \cdot C + I_b;$$

where $I_b$ is indicative of a holographic fluorescence spectral intensity of a calibration oil sample having an oil content of 0; C is indicative of an oil content of the current calibration oil sample; I is indicative of a holographic fluorescence spectral intensity of the current calibration oil sample; and a is indicative of a linear fit constant.

15. The computer device according to claim 12, characterized in that, the processor further executes the following steps when executing the computer program: obtaining an oil saturation of the rock sample to be measured according to the following equation:

$$S_o = V_o / (M_r / \rho_b \cdot \Phi) \cdot 100\%;$$

where $S_o$ is indicative of an oil saturation of a rock sample; $\rho_b$ is indicative of an apparent density of the rock (g/cm$^3$); $\Phi$ is indicative of a porosity of the rock; $V_o$ is indicative of an oil-containing volume of the rock sample to be measured (mL); and $M_r$ is indicative of mass of the rock sample to be measured.

16. A computer-readable storage medium, characterized in that, the computer-readable storage medium stores a computer program and the computer program comprises steps of:

measuring a plurality of calibration oil samples having different oil contents, and acquiring a holographic fluorescence spectral intensity corresponding to the calibration oil samples;

acquiring a fit relation between the holographic fluorescence spectral intensity and the oil contents of the calibration oil, according to the oil contents of the plurality of calibration oil samples and a plurality of holographic fluorescence spectral intensities corresponding thereto;

adding a certain amount of the calibration oil after dilution to rocks to be measured, and acquiring a sample of the rocks to be measured and performing a holographic fluorescence measurement of the rock sample to be measured; and introducing the holographic fluorescence spectral intensity of the rock sample to be measured to the fit relation, thus an oil content of the rock sample to be measured is obtained.

* * * * *